United States Patent [19]

Wiedmann et al.

[11] Patent Number: 5,747,001
[45] Date of Patent: May 5, 1998

[54] AEROSOLS CONTAINING BECLOMETHAZONE NANOPARTICLE DISPERSIONS

[75] Inventors: Timothy S. Wiedmann, Minneapolis, Minn.; Ray W. Wood, Ft. Washington; Lan DeCastro, West Chester, both of Pa.

[73] Assignee: NanoSystems, L.L.C., King of Prussia, Pa.

[21] Appl. No.: 393,973

[22] Filed: Feb. 24, 1995

[51] Int. Cl.$^6$ .................................................. A61K 9/12
[52] U.S. Cl. .................. 424/45; 424/46; 424/489
[58] Field of Search .................. 424/45, 46, 489; 514/826

[56] References Cited

U.S. PATENT DOCUMENTS

| | | | |
|---|---|---|---|
| 4,810,488 | 3/1989 | Jinks | 424/45 |
| 5,145,684 | 9/1992 | Liversidge et al. | 424/489 |
| 5,225,183 | 7/1993 | Purewal et al. | 424/45 |

FOREIGN PATENT DOCUMENTS 03153  2/1994  WIPO.

*Primary Examiner*—Raj Bawa
*Attorney, Agent, or Firm*—McDermott, Will & Emery

[57] ABSTRACT

There is disclosed an aerosol comprising droplets of an aqueous dispersion of nanoparticles, said nanoparticles comprising insoluble beclomethazone particles having a surface modifier on the surface thereof. There is also disclosed a method for making the aerosol and methods for treatment using the aerosol.

10 Claims, No Drawings

5,747,001

AEROSOLS CONTAINING BECLOMETHAZONE NANOPARTICLE DISPERSIONS

FIELD OF THE INVENTION

The present invention is directed to the field of nanoparticles and particularly beclomethazone containing nanoparticles in an aerosol form.

BACKGROUND OF THE INVENTION

Delivery of therapeutic agent to the respiratory tract is important for both local and systemic treatment of disease. With the conventional techniques, delivery of agents to the lung is extremely inefficient. Attempts to develop respirable aqueous suspensions of poorly soluble compounds have been unsuccessful. Micronized therapeutic agents suspended in aqueous media are too large to be delivered by aerosolized aqueous droplets. With conventional processes, it is estimated that only about 10 to 20% of the agent reaches the lung. Specifically, there is loss to the device used to deliver the agent, loss to the mouth and throat and with exhalation. These losses lead to variability in therapeutic agent levels and poor therapeutic control. In addition, deposition of the agent to the mouth and throat can lead to systemic absorption and undesirable side effects.

The efficiency of respiratory drug delivery is largely determined by the particle size distribution. Large particles (greater than 10 μm) are primarily deposited on the back of the throat. Greater than 60% of the particles with sizes between 1 and 10 μm pass with the air stream into the upper bronchial region of the lung where most are deposited. With particles less than about 1 μm, essentially all of the particles enter the lungs and pass into the peripheral alveolar region; however, about 70% are exhaled and therefore are lost.

In addition to deposition, the relative rate of absorption and rate of clearance of the therapeutic agent must be considered for determining the amount of therapeutic agent that reaches the site of action. Since 99.99% of the available area is located in the peripheral alveoli, rapid absorption can be realized with delivery of the particles to the periphery. For clearance, there is also differences between the central and peripheral regions of the lung. The peripheral alveolar region does not have ciliated cells but relies on macrophage engulfment for particle clearance. This much slower process can significantly extend the time during which the particles reside in the lung thereby enhancing the therapeutic or diagnostic effect. In contrast, particles deposited in the upper respiratory tract are rapidly cleared by mucociliary escalator. That is, the particles are trapped in the mucous blanket coating the lung surface and are transported to the throat. Hence, this material is either swallowed or removed by coughing.

While it has long been known that smaller droplets of an aerosol reach deeper into the respiratory system (*Current Concepts in the Pharmaceutical Sciences: Dosage and Bioavailability*, J. Swarbrick Ed., Lea and Febiger, Philadelphia, Pa., 1973, pp. 97–148) these have largely been of theoretical interest. Simply knowing that smaller droplets of aersol can be delivered deeper into the respiratory system does not solve the problem of incorporating sufficient therapeutic agent into the aerosol to be efficient, particularly where the therapeutic agent is only slightly soluble in the liquid for the aerosol.

Nanoparticles, described in U.S. Pat. No. 5,145,684, are particles consisting of a poorly soluble therapeutic or diagnostic agent onto which are adsorbed a non-crosslinked surface modifier, and which have an average particle size of less than about 400 nanometers (nm). However, no mention is made of attempts to nebulize (aerosolize or atomize are equivalent terms for the purpose of this disclosure) these compositions and it is not apparent that nebulizing these composition would provide useful aerosols or that there would be any advantage for doing so.

Beclomethazone dipropionate monohydrate is an antiinflamatory steroid that is commercially available in the form of a nasal spray. According to the Physicians' Desk Reference®, it is sparingly soluble and when given by nasal inhalation in the form of an aqueous or aerosolized suspension, the drug is deposited primarily in the nasal passages. A portion of the drug is swallowed. Thus, delivery of beclomethazone is prone to all of the problems known for aerosolized suspensions of slightly soluble drugs mentioned above.

SUMMARY OF THE INVENTION

In accordance with the present invention, there is provided an aerosol comprising droplets of an aqueous dispersion of nanoparticles, said nanoparticles comprising beclomethasone having a surface modifier on the surface thereof.

In another aspect of the invention, there is provided a method for forming an aerosol of a nanoparticle dispersion, said nanoparticles comprising beclomethasone particles having a surface modifier on the surface thereof, said method comprising the steps of:

a) providing a suspension of said nanoparticles;

b) nebulizing said suspension so as to form an aerosol.

In yet another aspect of the invention, there is provided a method of treating a mammal comprising the steps of:

a) forming an aerosol of an aqueous dispersion of nanoparticles, said nanoparticles comprising beclomethasone having a surface modifier on the surface thereof;

b) administering said aerosol to the respiratory system of said mammal.

DETAILED DESCRIPTION OF THE INVENTION

Beclomethazone dipropionate has the structural formula:

[structural formula of beclomethazone dipropionate with substituents $CH_2OCOC_2H_5$, $C=O$, $OCOC_2H_5$, $CH_3$, $HO$, $H$, $CH_3$, $Cl$, $H$]

It is a white powder with a molecular weight of 521.25; and is very slightly soluble in water. As used herein, the term beclomethazone means free beclomethazone; its various mono- and diesters. Specifically included is the preferred form, beclomethazone dipropionate and its monohydrate The compositions of the invention are aerosols. Aerosols can be defined for the present purpose as colloidal systems consisting of very finely divided liquid droplets dispersed in and surounded by a gas. The droplets in the aerosols typically have a size less than about 50 microns in diameter although droplets of a much smaller size are possible.

The aerosols of the present invention are particularly useful in the treatment of respiratory related illnesses.

Beclomethazone is particularly useful in the treatment of seasonal or perennial rhinitis and is also indicated for the relief of the symptoms of seasonal or perennial allergic an nonallergic (vasomotor) rhinitis.

The aerosols of the invention are made by nebulizing the nanoparticle containing solution using a variety of known nebulizing techniques. Perhaps the simplest of systems is the "two-phase" system which consists of a solution or a suspension of active ingredient, in the present case, a nanoparticle containing a beclomethazone, in a liquid propellent. Both liquid and vapor phases are present in a pressurized container and when a valve on the container is opened, liquid propellent containing the nanoparticle dispersion is released. Depending on the nature of the ingredients and the nature of the valve mechanism, a fine aersol mist or aersol wet spray is produced.

There are a variety of nebulisers that are available to produce the aerosols of the invention including small volume nebulizers. Compressor driven nebulizers incorporate jet technology and use compressed air to generate the aersol. Commercially available devices are available from Healthdyne Technologies Inc; Invacare Inc.; Mountain Medical Equipment Inc.; Pari Respiratory Inc.; Mada Mediacal Inc.; Puritan-Bennet; Schuco Inc.; Omron Healthcare Inc.; DeVilbiss Health Care Inc; and Hospitak Inc.

Ultrasonic nebulizers deliver high medication output and are used by patients suffering from severe asthma, or other severe respiratory related illnesses.

Surface Modifiers

Suitable surface modifiers can preferably be selected from known organic and inorganic pharmaceutical excipients. Such excipients include various polymers, low molecular weight oligomers, natural products and surfactants. Preferred surface modifiers include nonionic and ionic surfactants.

Representative examples of surface modifiers include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxy propylcellulose, hydroxypropylmethylcellulose phthalate, noncrystalline cellulose, magnesium aluminum silicate, triethanolamine, polyvinyl alcohol, and polyvinylpyrrolidone (PVP). Most of these surface modifiers are known pharmaceutical excipients and are described in detail in the Handbook of Pharmaceutical Excipients, published jointly by the American Pharmaceutical Association and The Pharmaceutical Society of Great Britain, the Pharmaceutical Press, 1986.

Particularly preferred surface modifiers include polyvinylpyrrolidone, tyloxapol, poloxamers such as Pluronic™ F68 and F108, which are block copolymer of ethylene oxide and propylene oxide, and polyxamines such as Tetronic™ 908 (also known as Poloxamine™ 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OT™, which is a dioctyl ester of sodium sulfosuccinic acid, available from American Cyanimid, Duponol™ P, which is a sodium lauryl sulfate, available from DuPont, Triton™ X-200, which is an alkyl aryl polyether sulfonate, available from Rohn and Haas, Tween™ 20 and Tween™ 80, which are polyoxyethylene sorbitan fatty acid esters, available from ICI Specialty Chemicals; Carbowax™ 3550 and 934, which are polyethylene glycols available from Union Carbide; Crodesta™ F-110, which is a mixture of sucrose stearate and sucrose distearate, available from Croda Inc., Crodesta™ SL-40, which is available from Croda, Inc., and SA90HCO, which is $C_{18}H_{37}—CH_2(CON(CH_3)CH_2(CHOH)_4CH_2OH)_2$. Surface modifiers which have been found to be particularly useful include Tetronic™ 908, the Tweens™, Pluronic™ F-68 and polyvinylpyrrolidone. Other useful surface modifiers include:

decanoyl-N-methylglucamide;
n-decyl β-D-glucopyranoside;
n-decyl β-D-maltopyranoside;
n-dodecyl β-D-glucopyranoside;
n-dodecyl β-D-maltoside;
heptanoyl-N-methylglucamide;
n-heptyl-β-D-glucopyranoside;
n-heptyl β-D-thioglucoside; n-hexyl β-D-glucopyranoside;
nonanoyl-N-methylglucamide;
n-noyl β-D-glucopyranoside;
octanoyl-N-methylglucamide;
n-octyl-β-D-glucopyranoside;
octyl β-D-thioglucopyranoside; and the like.

Another useful surface modifier is tyloxapol (a nonionic liquid polymer of the alkyl aryl polyether alcohol type; also known as superinone or triton). This surface modifier is commercially available and/or can be prepared by techniques known in the art.

Another preferred surface modifier is p-isononylphenoxypoly(glycidol) also known as Olin-10G™ or Surfactant 10-G, is commercially available as 10G™ from Olin Chemicals, Stamford, Conn.

Non-Ionic Surface Modifiers

Preferred surface modifiers can be selected from known non-ionic surfactants, including the poloxamines such as Tetronic™ 908 (also known as Poloxamine™ 908), which is a tetrafunctional block copolymer derived from sequential addition of propylene oxide and ethylene oxide to ethylenediamine, available from BASF, or Tetronic™ 1508 (T-1508), or a polymer of the alkyl aryl polyether alcohol type, such as tyloxapol.

The surface modifiers are commercially available and/or can be prepared by techniques known in the art. Two or more surface modifiers can be used in combination.

Tyloxapol

Tyloxapol (4-(1,1,3,3-tetramethylbutyl)-phenol polymer with ethylene oxide and formaldehyde) is a preferred surface modifier and is a nonionic liquid polymer of the alkyl aryl polyether alcohol type. Tyloxapol, also known as "Superinone", is disclosed as useful as a nonionic surface active agent in a lung surfactant composition in U.S. Pat. No. 4,826,821 and as a stabilizing agent for 2-dimethylaminoethyl 4-n-butylaminobenzoate in U.S. Pat. No. 3,272,700.

Tyloxapol may be associated with the nanoparticles and may function as a surface modifier, as a stabilizer, and/or as a dispersant. Alternatively, the tyloxapol may serve other purposes. Tyloxapol may serve all three functions. The tyloxapol may serve as a stabilizer and/or a dispersant, whereas another compound acts as a surface modifier.

Auxiliary Surface Modifiers Particularly preferred auxiliary surface modifiers are those which impart resistance to particle aggregation during sterilization and include dioctylsulfosuccinate (DOSS), polyethylene glycol, glycerol, sodium dodecyl sulfate, dodecyl trimethyl, ammonium bromide and a charged phospholipid such as dimyristoyl phophatidyl glycerol. The surface modifiers are commercially available and/or can be prepared by techniques known in the art. Two or more surface modifiers can be used in combination.

Block Copolymer Surface Modifiers

One preferred surface modifier is a block copolymer linked to at least one anionic group. The polymers contain at least one, and preferably two, three, four or more anionic groups per molecule. Preferred anionic groups include sulfate, sulfonate, phosphonate, phosphate and carboxylate groups. The anionic groups are covalently attached to the nonionic block copolymer. The nonionic sulfated polymeric surfactant has a molecular weight of 1,000–50,000, preferably 2,000–40,000 and more preferably 3,000–30,000. In preferred embodiments, the polymer comprises at least about 50%, and more preferably, at least about 60% by weight of hydrophilic units, e.g., alkylene oxide units. The reason for this is that the presence of a major weight proportion of hydrophilic units confers aqueous solubility to the polymer.

A preferred class of block copolymer useful as surface modifiers herein includes sulfated block copolymers of ethylene oxide and propylene oxide. These block copolymer in an unsulfated form are commercially available as Pluronics™. Specific examples of the unsulfated block copolymer include F68, F108 and F127.

Another preferred class of block copolymer useful herein include tetrafunctional block copolymer derived from sequential addition of ethylene oxide and propylene oxide to ethylene diamine. These polymers, in an unsulfated form, are commercially available as Tetronics™.

Another preferred class of surface modifiers contain at least one polyethylene oxide (PEO) block as the hydrophilic portion of the molecule and at least one polybutylene oxide (PBO) block as the hydrophobic portion. Particularly preferred surface modifiers of this class are diblock, triblock, and higher block copolymer of ethylene oxide and butylene oxide, such as are represented, for example, by the following structural formula: –(PEO)– –(PBO)–; –(PEO)– –(PBO)– –(PEO)–; and –(PEO)– –(PBO)– –(PEO)– –(PBO)–. The block copolymer useful herein are known compounds and/or can be readily prepared by techniques well known in the art.

Highly preferred surface modifiers include triblock copolymer of the structure –(PEO)– –(PBO)– –(PEO)– having molecular weights of 3800 and 5000 which are commercially available from Dow Chemical, Midland, Mich., and are referred to as B20-3800 and B20-5000. These surface modifiers contain about 80% by weight PEO. In a preferred embodiment, the surface modifier is a triblock polymer having the structure:

$$R-Q+CH_2CH_2O\}_x\left[\begin{array}{c}CH_2CHO\\|\\C_2H_5\end{array}\right]_y+CH_2CH_2O\}_z Q-R$$

Q is an anionic group
wherein R is H or a metal cation such as $Na^+$, $K^+$ and the like, x is 15–700, y is 5–200 and z is 15–700.

Grinding

The described particles can be prepared in a method comprising the steps of dispersing beclomethazone in a liquid dispersion medium and applying mechanical means in the presence of grinding media to reduce the particle size of the beclomethazone to an effective average particle size of less than about 400 nm. The particles can be reduced in size in the presence of a surface modifier. Alternatively, the particles can be contacted with a surface modifier after, attrition.

The beclomethazone is obtained commercially and/or prepared by techniques known in the art in a conventional coarse form. It is preferred, but not essential, that the particle size of the coarse beclomethazone selected be less than about 100 μm as determined by sieve analysis. If the coarse particle size of the beclomethazone is greater than about 100 μm, then it is preferred that the particles of the beclomethazone be reduced in size to less than 100 μm using a conventional milling method such as airjet or fragmentation milling.

The coarse beclomethazone selected can then be added to a liquid medium in which it is essentially insoluble to form a premix. The concentration of the beclomethazone in the liquid medium can vary from about 0.1–60%, and preferably is from 5–30% (w/w). It is preferred, but not essential, that the surface modifier be present in the premix. The concentration of the surface modifier can vary from about 0.1 to about 90%, and preferably is 1–75%, more preferably 20–60%, by weight based on the total combined weight of the beclomethazone and surface modifier. The apparent viscosity of the premix suspension is preferably less than about 1000 centipoise.

The premix can be used directly by subjecting it to mechanical means to reduce the average particle size in the dispersion to less than 400 nm. It is preferred that the premix be used directly when a ball mill is used for attrition. Alternatively, the beclomethazone and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the particle size of the beclomethazone conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

Preparation Conditions

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the beclomethazone. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Control of the temperature, e.g., by jacketing or immersion of the milling chamber in ice water are contemplated. Processing pressures from about 1 psi (0.07 kg/cm$^2$) up to about 50 psi (3.5 kg/cm$^2$) are contemplated. Processing pressures from about 10 psi (0.7 kg/cm$^2$) to about 20 psi (1.4 kg/cm$^2$) are typical.

The surface modifier, if it was not present in the premix, must be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

After attrition is completed, the grinding media is separated from the milled particulate product (in either a dry or liquid dispersion form) using conventional separation techniques, such as by filtration, sieving through a mesh screen, and the like.

Grinding Media

The grinding media for the particle size reduction step can be selected from rigid media preferably spherical or particulate in form having an average size less than about 3 mm and, more preferably, less than about 1 mm. Such media desirably can provide the particles with shorter processing times and impart less wear to the milling equipment. The selection of material for the grinding media is not believed to be critical. We have found that zirconium oxide, such as 95% ZrO$_2$ stabilized with magnesia, zirconium silicate, and glass grinding media provide particles having levels of contamination which are believed to be acceptable for the preparation of pharmaceutical compositions. However, other media, such as stainless steel, titania, alumina, and 95% ZrO$_2$ stabilized with yttrium, are expected to be useful. Preferred media have a density greater than about 3 g/cm$^3$.

Polymeric Grinding Media

The grinding media can comprise particles, preferably substantially spherical in shape, e.g., beads, consisting essentially of polymeric resin. Alternatively, the grinding media can comprise particles comprising a core having a coating of the polymeric resin adhered thereon.

In general, polymeric resins suitable for use herein are chemically and physically inert, substantially free of metals, solvent and monomers, and of sufficient hardness and friability to enable them to avoid being chipped or crushed during grinding. Suitable polymeric resins include crosslinked polystyrenes, such as polystyrene crosslinked with divinylbenzene, styrene copolymer, polycarbonates, polyacetals, such as Delrin™, vinyl chloride polymers and copolymer, polyurethanes, polyamides, poly(tetrafluoroethylenes), e.g., Teflon™, and other fluoropolymers, high density polyethylenes, polypropylenes, cellulose ethers and esters such as cellulose acetate, polyhydroxymethacrylate, polyhydroxyethyl acrylate, silicone containing polymers such as polysiloxanes and the like. The polymer can be biodegradable. Exemplary biodegradable polymers include poly(lactides), poly(glycolide) copolymer of lactides and glycolide, polyanhydrides, poly(hydroxyethyl methacylate), poly(imino carbonates), poly(N-acylhydroxyproline)esters, poly(N-palmitoyl hydroxyproline) esters, ethylene-vinyl acetate copolymer, poly(orthoesters), poly(caprolactones), and poly(phosphazenes). In the case of biodegradable polymers, contamination from the media itself advantageously can metabolize in vivo into biologically acceptable products which can be eliminated from the body.

The polymeric resin can have a density from 0.8 to 3.0 g/cm$^3$. Higher density resins are preferred inasmuch as it is believed that these provide more efficient particle size reduction.

The media can range in size from about 0.1 to 3 mm. For fine grinding, the particles preferably are from 0.2 to 2 mm, more preferably, 0.25 to 1 mm in size.

In a particularly preferred method, a beclomethazone is prepared in the form of submicron particles by grinding the agent in the presence of a grinding media having a mean particle size of less than about 75 microns.

The core material of the grinding media preferably can be selected from materials known to be useful as grinding media when fabricated as spheres or particles. Suitable core materials include zirconium oxides (such as 95% zirconium oxide stabilized with magnesia or yttrium), zirconium silicate, glass, stainless steel, titania, alumina, ferrite and the like. Preferred core materials have a density greater than about 2.5 g/cm$^3$. The selection of high density core materials is believed to facilitate efficient particle size reduction.

Useful thicknesses of the polymer coating on the core are believed to range from about 1 to about 500 microns, although other thicknesses outside this range may be useful in some applications. The thickness of the polymer coating preferably is less than the diameter of the core.

The cores can be coated with the polymeric resin by techniques known in the art. Suitable techniques include spray coating, fluidized bed coating, and melt coating. Adhesion promoting or tie layers can optionally be provided to improve the adhesion between the core material and the resin coating. The adhesion of the polymer coating to the core material can be enhanced by treating the core material to adhesion promoting procedures, such as roughening of the core surface, corona discharge treatment, and the like.

Continuous Grinding

In a preferred grinding process, the particles are made continuously rather than in a batch mode. The continuous method comprises the steps of continuously introducing the beclomethazone and rigid grinding media into a milling chamber, contacting the agent with the grinding media while in the chamber to reduce the particle size of the agent, continuously removing the agent and the grinding media from the milling chamber, and thereafter separating the agent from the grinding media.

The beclomethazone and the grinding media are continuously removed from the milling chamber. Thereafter, the grinding media is separated from the milled particulate agent (in either a dry or liquid dispersion form) using conventional separation techniques, in a secondary process such as by simple filtration, sieving through a mesh filter or screen, and the like. Other separation techniques such as centrifugation may also be employed.

In a preferred embodiment, the agent and grinding media are recirculated through the milling chamber. Examples of suitable means to effect such recirculation include conventional pumps such as peristaltic pumps, diaphragm pumps, piston pumps, centrifugal pumps and other positive displacement pumps which do not use sufficiently close tolerances to damage the grinding media. Peristaltic pumps are generally preferred.

Another variation of the continuous process includes the use of mixed media sizes. For example, larger media may be employed in a conventional manner where such media is restricted to the milling chamber. Smaller grinding media may be continuously recirculated through the system and permitted to pass through the agitated bed of larger grinding media. In this embodiment, the smaller media is preferably between about 1 and 300 mm in mean particle size and the larger grinding media is between about 300 and 1000 mm in mean particle size.

Precipitation Method

Another method of forming the desired nanoparticle dispersion is by microprecipitation. This is a method of preparing stable dispersions of beclomethazone in the presence of a surface modifying and colloid stability enhancing surface active agent free of trace of any toxic solvents or solubilized heavy metal impurities by the following procedural steps:

1. Dissolving the beclomethazone in aqueous base with stirring,
2. Adding above #1 formulation with stirring to a surface active surfactant (or surface modifiers) solution to form a clear solution, and,
3. Neutralizing above formulation #2 with stirring with an appropriate acid solution. The procedure can be followed by:
4. Removal of formed salt by dialysis or diafiltration and
5. Concentration of dispersion by conventional means.

This microprecipitation process produces dispersion of beclomethazone with Z-average particle diameter less than 400 nm (as measured by photon correlation spectroscopy) that are stable in particle size upon keeping under room temperature or refrigerated conditions. Such dispersions also demonstrate limited particle size growth upon autoclave-decontamination conditions used for standard blood-pool pharmaceutical agents.

Step 3 can be carried out in semicontinuous, continuous batch, or continuous methods at constant flow rates of the reacting components in computer-controlled reactors or in tubular reactors where reaction pH can be kept constant using pH-stat systems. Advantages of such modifications are that they provide cheaper manufacturing procedures for large-scale production of nanoparticulate dispersion systems.

Additional surface modifier may be added to the dispersion after precipitation. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

In a preferred embodiment, the above procedure is followed with step 4 which comprises removing the formed salts by diafiltration or dialysis. This is done in the case of dialysis by standard dialysis equipment and by diafiltration using standard diafiltration equipment known in the art. Preferably, the final step is concentration to a desired concentration of the agent dispersion. This is done either by diafiltration or evaporation using standard equipment known in this art.

An advantage of microprecipitation is that unlike milled dispersion, the final product is free of heavy metal contaminants arising from the milling media that must be removed due to their toxicity before product is formulated.

A further advantage of the microprecipitation method is that unlike solvent precipitation, the final product is free of any trace of trace solvents that may be toxic and must be removed by expensive treatments prior to final product formulation.

In another preferred embodiment of the microprecipitation process, a crystal growth modifier is used. A crystal growth modifier is defined as a compound that in the co-precipitation process incorporates into the crystal structure of the microprecipitated crystals of the beclomethazone, thereby hindering growth or enlargement of the microcrystalline precipitate, by the so called Ostwald ripening process. A crystal growth modifier (or a CGM) is a chemical that is at least 75% identical in chemical structure to the beclomethazone. By "identical" is meant that the structures are identical atom for atom and their connectivity. Structural identity is characterized as having 75% of the chemical structure, on a molecular weight basis, identical to the beclomethazone. The remaining 25% of the structure may be absent or replaced by different chemical structure in the CGM. The crystal growth modifier is dissolved in step #1 with the beclomethazone.

Particle Size

As used herein, particle size refers to a number average particle size as measured by conventional particle size measuring techniques well known to those skilled in the art, such as sedimentation field flow fractionation, photon correlation spectroscopy, or disk centrifugation. When photon correlation spectroscopy (PCS) is used as the method of particle sizing the average particle diameter is the Z-average particle diameter known to those skilled in the art. By "an effective average particle size of less than about 400 nm" it is meant that at least 90% of the particles have a weight average particle size of less than about 400 nm when measured by the above-noted techniques. In preferred embodiments, the effective average particle size is less than about 300 nm and more preferrably less than about 250 nm. In some embodiments, an effective average particle size of less than about 100 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

Ratios

The relative amount of beclomethazone and surface modifier can vary widely and the optimal amount of the surface modifier can depend on surface modifier selected, the critical micelle concentration of the surface modifier if it forms micelles, the hydrophilic lipophilic balance (HLB) of the stabilizer, the melting point of the stabilizer, its water solubility, the surface tension of water solutions of the stabilizer, etc. The surface modifier preferably is present in an amount of about 0.1–10 mg per square meter surface area of the beclomethazone. The surface modifier can be present in an amount of 0.1–90%, preferably 20–60% by weight based on the total weight of the dry particle.

The following examples are presented for a further understanding of the invention.

EXAMPLE 1

Materials

Beclomethasone diproprionate (BDP) and polyvinyl alcohol (PVA) were obtained from Sigma Chemical Co. (St. Louis, Mo.) and used as received. All other chemicals were analytical/reagent grade or better.

Nanoparticle Preparation and Characterization

Nanoparticles were prepared by media milling a suspension of 5% beclomethasone diproprionate in an aqueous solutions of PVA. Thus, the PVA was the surface modifier. The resulting particle size distribution was determined by dynamic light scattering. The particle size distribution was periodically monitored throughout the course of the study.

Nebulization A gas cylinder of compressed air was used as the source, which was equipped with a pressure regulator. Oxygen connecting tubing joined from the regulator to the Puritan-Bennet Raindrop nebulizer (Lenexa, KA). One exit port of the T-connector of the nebulizer was blocked with a #2 rubber stopper. The other exit port was fitted with Tygon tubing (½" id). This in turn led initially to a calibrated flow meter from which the flow rate was set before each experiment. After calibration, the gas flow was stopped by shutting off the main cylinder valve. The flow meter was removed, and the nebulizer was connected to a Y-tube with 24/40 joints by tubing (½" id, 6" length). The Y-tube was connected to the cascade impactor (Andersen Mark I, Andersen Samplers Ind. Atlanta, Ga.) by a constructed stainless steel adapter consisting of a tapered side that fit within the 24/40 ground glass joint and a cylindrical section with rubber o-ring gasket that fit into the top of the cascade impactor. The air flow rate through the impactor was drawn by a vacuum pump and regulated by a calibrated flow meter to the recommended 28.3 L/min.

Preliminary studies indicated that pressures between 20 and 40 psig had little effect on either the performance of the nebulizer or the resulting aerosol size distribution. Thus, the pressure was kept constant at 40 psig. Studies of the effect of flow rate on nebulizer performance and aerosol size distribution were also conducted. As the flow rate was decreased from 5 to 2 L/min, aerosol particles had progressively larger mean aerodynamic diameter. At a flow rate 8 L/min, there was excessive foaming. Thus, all studies were conducted at a flow rate of 6 L/min.

Suspension and Nanoparticle Nebulization

Formulations for nebulization consisted of a 0.2% beclomethasone diproprionate dispersions with PVA. The nebulizers contained either a volume of 2 mL or 6 mL. Two concentrations of PVA were used which were prepared by diluting the original 5% (w/v) nanoparticle dispersion with a PVA solution having the same PVA concentration as the original dispersion concentration or with water. The nebulizer was filled, and aliquots of the solution were taken for subsequent determination of drug concentration. The weight was also determined. The nebulization process was initiated by opening the valve on the main gas cylinder, and the length of time until foaming or sputtering of the nebulizer was determined, and additional aliquots were taken for analysis. The fraction of mass exiting the nebulizer was calculated from the weight difference of the nebulizer before and after nebulization. This was coupled with the time required for nebulization of the dispersion to yield the mass output rate in terms of the milliliters of dispersion nebulized/ unit time and the nebulizer output in terms of the volume of dispersion nebulized/liter of air were determined.

Aliquots taken from the nebulizer were diluted with 50% (v/v) ethanol in water, and the absorbance determined at 240 nm. With measurement of the absorbance of appropriate standards, the concentration of BDP was calculated. From the masses of the nebulizer before and after nebulization and the BDP concentrations, the fraction of BDP remaining in the nebulizer was calculated. The mass of BDP collected on the cascade impactor and the aerosol particle size distribution was determined by extracting the impactor stages with 10 mL of the ethanol/water solution. Aliquots were taken and the absorbances and subsequent concentration were determined. The mass median aerodynamic diameter and geometric standard deviation of the particle distribution was obtained by plotting the cumulative mass on the stages of the impactor as a function of the log of the cut-off diameter.

With the cumulative mass determined from the cascade impactor and the initial amount of BDP placed in the nebulizer, the fraction of BDP reaching the impactor was calculated.

To assess the fractionation of the dispersion, the nanoparticles and suspensions were diluted with PVA solutions containing 0.1% sodium fluorescein. Nebulization was conducted as described above. Since fluorescein has significant absorbance at both 490 and 240 nm while BDP has absorbance only at 240 nm, the absorbance of the diluted aliquots was determined at these two wavelengths. The concentration of fluorescein was determined from the absorbance at 490 nm and the measured absorptivity. In determining the concentrations of BDP, the contribution from the absorbance of fluorescein at 240 nm was subtracted based on the absorbance determined at 490 and the correction for the differences in the absorptivity at these two wavelengths.

Scanning Electron Microscopy

SEM was performed on nanoparticles after nebulization. Two dispersions were prepared containing 0.1 and 2.5% surfactant. These were placed in the nebulizer and 2 cm rectangular glass microscope slides were placed on every stage of the impactor. The glass slides were removed and sputtered with platinum. Micrographs were obtained with a JEOL 840-II ElectroScan Environmental ESEM (Peabody, Mass.).

RESULTS

Nanoparticles of beclomethasone diproprionate in 2.5% polyvinyl alcohol had a particle size distribution of 0.26±0.13 μm. This size remained constant throughout the course of the study; neither was there any evidence of chemical instability. In addition, particle size of the diluted dispersions remained constant for at least the duration of the experiment.

For nebulization, four formulations were tested. These are listed in Table I. The first was a suspension of raw drug substance BDP in 2.5% surfactant with a volume of 2 mL. The second was composed of a dispersion of nanoparticles thereby allowing direct comparison to the suspension formulation. The third was also a colloidal dispersion, but the surfactant concentration was smaller at 0.1%. The fourth was similar to the third but contained a larger volume of 6 mL.

In Table II, the results from the nebulization of the four formulations were given. The second column provides the mass output rate which was the rate at which the total mass of the dispersion exists the nebulizer. Formulations I and II are similar as were formulations III and IV. The difference between these two sets of formulations is that I and II had a surfactant concentration of 2.5%, whereas III and IV had a surfactant concentration of 0.1%.

The third column reflects the total mass fraction of dispersion remaining in the nebulizer. The fraction of mass remaining was between 0.27 and 0.69 indicating considerable amount of material remained in the nebulizer. In addition, formulations I, II and III were similar, but formulation IV had a significantly lower mass fraction remaining in the nebulizer. Formulation IV is distinct from the others in that it contained an initial volume of 6 mL.

In the next column, the fraction of BDP remaining in the nebulizer is given. These fractions ranged from 0.29 to 0.89. In comparing the fractions remaining, formulation I, which contained the suspension, had about 90% of BDP remain in the nebulizer. In contrast, formulation III which contained 0.1% surfactant, had a significantly lower fraction of BDP remain in the nebulizer. An even more dramatic drop in fraction remaining was observed with formulation IV which had a low surfactant concentration as well as a larger volume.

It is also noteworthy to compare the fraction of BDP remaining relative to the fraction of total mass remaining in the nebulizer. With formulation I, there was a significantly greater fraction of BDP relative to the total mass remaining. Numerically this is also true for formulation II: however, there was more variability in these measurements which had no statistical difference in the fractions remaining. In formulations III and IV, there was no difference.

The fraction of BDP reaching the nebulizer is also given in Table II. It is seen that only about 7% of the BDP presented as a suspension or raw drug substance reaches the impactor. In comparison, the use of nanoparticles led to a significantly higher fraction reaching the impactor. These ranged from 0.17 to over 0.34. In formulations II and III which contained 2 mL of dispersion, about 18% of BDP reached the impactor. In the large volume formulation IV, almost 35% of BDP reached the impactor.

Finally, it is evident that the amount of BDP that was originally placed in the nebulizer should equal the amount of BDP remaining in the nebulizer added to the amount of BDP on the impactor. Expressing the mass balance in terms of fractions, the fraction of BDP remaining in the nebulizer plus the fraction of BDP on the impactor should equal unity. As can be deduced from the fractions given in Table II, this was only the case with formulation II. In other cases, there was a net loss of BDP. In particular, for formulation III, only 80% of BDP was accounted for, and in formulation IV, the percent accounted for dropped to about 60%.

It is evident when the fraction of BDP collected on the impactor stage is plotted as a function of the cut-off diameter of the stage that suspensions of raw drug substance have a distribution of particles with a larger size and its distribution is more polydisperse. The nanoparticles have particles size distributions with 80% of the particles being less than 2.5 μm.

In Table III, the results from the fluorescein study are given. In comparing the mass exited, both formulations gave similar results of about 0.75. There was also no significant difference between the fractions of BDP and fluorescein remaining in the nebulizer. For the suspension, the fraction of BDP and fluorescein remaining were 88 and 89%, respectively. For the nanoparticles, the percents were 81 and 85 which are not statistically different from each other. In addition, there was no statistical difference in the fractions of BDP and fluorescein remaining in the nebulizer between formulations I and II. However, the fractions of BDP and fluorescein remaining are significantly greater than the fraction of total mass remaining for the suspension and nanoparticle formulations.

The fractions of BDP reaching the impactor were different between the two formulations. For the suspension, the fraction of fluorescein collected on the impactor was almost twice as high as the fraction of BDP. For the nanoparticles, the fraction of fluorescein was similar to that found with suspensions. The fraction of BDP collected on the impactor was much higher than observed with suspensions, but slightly less than that observed with fluorescein.

The final study was an examination of the particles after being subjected to the process of nebulization. Scanning electron microscopy was conducted of the nanoparticles deposited on the sixth stage of the impactor for the 2.5 and 0.1% nanoparticles

TABLE I

Formulation Components

| Formulation | Form | [Surfactant] | Volume (mL) |
|---|---|---|---|
| I | Suspension | 2.5% | 1.85 |
| II | Nanoparticle Dispersion | 2.5% | 1.85 |
| III | Nanoparticle Dispersion | 0.1% | 1.85 |
| IV | Nanoparticle Dispersion | 0.1% | 5.85 |

Formulation "I" is a comparative formulation not using nanoparticles.

TABLE II

Comparison of Nebulization Output Parameters as a Function of Formulate Effect of Nebulization Process on Resulting Aerosol Production. Results are expressed as the mean ± standard deviation, n = 3.

| Formulation | Mass output rate (mg/sec) | Mass fraction remain. | BDP fraction remain. | BDP fraction on impactor |
|---|---|---|---|---|
| I | 2.73 ± 0.5 | 0.69 ± 0.036 | 0.89 ± 0.013 | 0.082 ± 0.012 |
| II | 2.61 ± 0.14 | 0.51 ± 0.15 | 0.768 ± 0.23 | 0.184 ± 0.47 |
| III | 4.99 ± 0.31 | 0.67 ± 0.006 | 0.618 ± 0.025 | 0.174 ± 0.019 |
| IV | 4.35 ± 0.65 | 0.27 ± 0.015 | 0.289 ± 0.039 | 0.345 ± 0.15 |

TABLE III

Comparison of the nebulization of nanoparticle dispersions and suspensions of BDP containing a solution of fluorescein. Results are expressed as the mean ± deviation, n = 3.

| Formulation | Mass fraction remaining | BDP fraction remaining | Fluorescein fraction remaining | BDP fraction on impactor | Fluorescein fraction on impactor |
|---|---|---|---|---|---|
| Suspension | 0.76 ± 0.06 | 0.88 ± 0.046 | 0.89 ± 0.13 | 0.067 ± 0.02 | 0.122 ± 0.033 |
| Nanoparticles | 0.74 ± 0.017 | 0.81 ± 0.088 | 0.85 ± 0.065 | 0.11 ± 0.016 | 0.143 ± 0.020 |

We claim:

1. An aerosol of an aqueous dispersion of nanoparticles, wherein the nanoparticles comprise 0.1 to 60% (w/w) of insoluble beclomethasone particles having (1) an average particle size of less than about 400 nm, and (2) 0.1 to 90% (w/w) of a surface modifier adsorbed on the surface thereof.

2. An aerosol according to claim 1; wherein said surface modifier is selected from the group consisting of polyvinyl alcohol, polyvinylpyrrolidone tyloxapol, a polyoxamer, a polyoxamine dextran lecithin a dialkylester of sodium sulfosuccinic acid, sodium lauryl sulfate, an alkyl aryl polyether sulfonate, a polyoxyethylene sorbitan fatty acid ester, polyethylene glycol, a mixture of sucrose stearate and sucrose distearate, $C_{18}H_{37}CH_2(CON(CH_3)CH_2(CHOH)_4(CH_2OH)_2$, carboxymethylcellulose calcium, carboxymethylcellulose sodium, methylcellulose, hydroxyethylcellulose, hydroxy propylcellulose, hydroxypropylmethylcellulose phthalate, noncrystalline cellulose, and isononylphenoxypoly(glycidol).

3. A method for forming an aerosol of an aqueous dispersion of nanoparticles, said nanoparticles comprising insoluble beclomethasone particles comprising:

a) providing an aqueous suspension of nanoparticles, wherein the nanoparticles comprise 0.1 to 60% (w/w) of insoluble beclomethasone particles having (1) an average particle size of less than about 400 nm, and (2) 0.1 to 90% (w/w) of a surface modifier adsorbed on the surface thereof; and b) nebulizing said suspension so as to form an aerosol.

4. A method of treating a respiratory related illness of a mammal comprising:

administering an effective amount of an aerosol comprising an aqueous dispersion of nanoparticles, wherein said nanoparticles comprise 0.1 to 60% (w/w) of insoluble beclomethasone particles having (1) an average particle size of less than about 400 nm, and (2) 0.1 to 90% of a surface modifier adsorbed on the surface thereof, wherein droplets of the aerosol deposit in the respiratory tract of the mammal.

5. A method according to claim 4, wherein droplets of the aerosol deposit in the lung of the mammal.

6. The aerosol according to claim 1 or 2, wherein the beclomethasone particles are beclomethasone dipropionate particles.

7. The method according to any one of claims 3, 4, or 5, wherein the beclomethasone particles are beclomethasone dipropionate particles.

8. The method according to claim 3, wherein the surface modifier is selected from the group consisting of polyvinyl alcohol, polyvinylpyrrolidone, tyloxapol, a polyoxamer, a polyoxamine, dextran, lecithin, a dialkylester of sodium sulfosuccinic acid, sodium lauryl sulfate, an alkyl aryl polyether sulfonate, a polyoxyethylene sorbitan fatty acid ester, polyethylene glycol, a mixture of sucrose stearate and sucrose distearate, $C_{18}H_{37}CH_2(CON(CH_3)CH_2(CHOH)_4$-$(CH_2OH)_2$, carboxymethylcellulose calcium, carboxymethylcellulose sodium, methylcellulose, hydroxyethylcellulose, hydroxy propylcellulose, hydroxypropylmethylcellulose phthalate, noncrystalline cellulose, and isononylphenoxypoly(glycidol).

9. The method according to claim 4, wherein the surface modifier is selected from the group consisting of polyvinyl alcohol, polyvinylpyrrolidone, tyloxapol, a polyoxamer, a polyoxamine, dextran, lecithin, a dialkylester of sodium sulfosuccinic acid, sodium lauryl sulfate, an alkyl aryl polyether sulfonate, a polyoxyethylene sorbitan fatty acid ester, polyethylene glycol, a mixture of sucrose stearate and sucrose distearate, $C_{18}H_{37}CH_2(CON(CH_3)CH_2(CHOH)_4$-$(CH_2OH)_2$, carboxymethylcellulose calcium, carboxymethylcellul hydroxyethylcellulose, hydroxy propylcellulose, hydroxypropylmethylcellulose phthalate, noncrystalline cellulose, and isononylphenoxypoly(glycidol).

10. The method according to claim 4, wherein the respiratory related illness is selected from the group consisting of seasonal rhinitis, perennial rhinitis, seasonal allergic (vasomotor) rhinitis, seasonal nonallergic (vasomotor) rhinitis, perennial allergic (vasomotor) rhinitis, and perennial nonallergic (vasomotor) rhinitis.

* * * * *